United States Patent [19]

Hartley et al.

[11] Patent Number: 5,106,727
[45] Date of Patent: Apr. 21, 1992

[54] AMPLIFICATION OF NUCLEIC ACID SEQUENCES USING OLIGONUCLEOTIDES OF RANDOM SEQUENCES AS PRIMERS

[75] Inventors: James L. Hartley, Frederick; Mark S. Berninger, Gaithersburg, both of Md.

[73] Assignee: Life Technologies, Inc., Gaithersburg, Md.

[21] Appl. No.: 552,407

[22] Filed: Jul. 13, 1990

Related U.S. Application Data

[63] Continuation-in-part of Ser. No. 344,674, Apr. 27, 1989, Pat. No. 5,043,272.

[51] Int. Cl.$^5$ .................. C12Q 1/68; C12P 19/34; G01N 33/48; G01N 33/566
[52] U.S. Cl. .................................. 435/6; 435/5; 435/91; 435/810; 436/501; 436/94; 935/77; 935/78
[58] Field of Search ................ 435/5, 6, 91, 94; 436/501; 536/26, 27, 28; 935/77, 78

[56] References Cited

U.S. PATENT DOCUMENTS 4,683,202 7/1987 Mullis ............................ 435/6

OTHER PUBLICATIONS

Maniatis et al., Molecular Cloning: A Lab. Manual, Cold Spring Harbor, N.Y. (1982).
Shibata et al., J. Exp. Med. 167:225–230, Jan. 1988).

*Primary Examiner*—Margaret Moskowitz
*Assistant Examiner*—Stephanie W. Zitomer
*Attorney, Agent, or Firm*—Sterne, Kessler, Goldstein & Fox

[57] ABSTRACT

According to this invention, a process for substantially amplifying template nucleic acid present in a sample is described, wherein said amplification may be performed without prior knowledge of specific sequences, which process comprises apposition of random oligonucleotide primers to said template nucleic acid under conditions such that extension products of said primers are synthesized which are complementary to said template nucleic acid.

5 Claims, No Drawings

AMPLIFICATION OF NUCLEIC ACID SEQUENCES USING OLIGONUCLEOTIDES OF RANDOM SEQUENCES AS PRIMERS

RELATED APPLICATIONS

This application is a continuation-in-part of U.S. patent application Ser. No. 07/344,674, filed Apr. 27, 1989, now U.S. Pat. No. 5,043,272 issued Aug. 27, 1991.

FIELD OF THE INVENTION

The present invention is in the field of recombinant DNA technology. This invention is directed to a process of random priming amplification of nucleic acid sequences.

BACKGROUND OF THE INVENTION

It is desirable for many purposes to increase (amplify) the amount of a nucleic acid sequence present in a sample. Detection and cloning of specific genomic or nucleic acid targets is limited by the ability to obtain sufficient starting material or by the abundance of the target sequence. Detection of a specific nucleic acid sequence is important in many fields and especially in clinical diagnostics, forensics, environmental and foodstuff monitoring and biological research.

It is known to prime reverse transcriptase in a random, non-specific manner for the synthesis of cDNA from mRNA (Noonan K. E. et al., *Nucl. Acids Res.* 16: 10366 (1988)). Noonan et al. disclose a method of mRNA phenotyping which combines reverse transcription of mRNA with polymerase chain reaction (PCR) amplification (infra) of the desired targets. The reverse transcriptase reaction was primed with random hexadeoxyribonucleotides rather than with the more commonly used oligo-dT primer so as to minimize the effects of sequence complexity, mRNA secondary structure and varying lengths of poly A tails. However, although reverse transcriptase was able to synthesize primary transcripts using primers of a random sequence, it was still necessary to amplify the specific cDNA product of interest with PCR for further analysis.

It is also known to prime DNA polymerase with oligonucleotides in a random non-specific manner for the synthesis of labelled or derivatized DNA probes for use in the detection of other nucleic acid sequences (Feinberg, A. P. et al., *Anal. Biochem.* 132:6-13 (1983); Liang, W. et al., *Nucl. Acids Res.* 16:3579 (1988)). According to this technique, DNA is first denatured by heating, so that the double stranded DNA becomes single stranded, and then random hexanucleotide primers are added, together with deoxynucleoside triphosphates, buffer, the Klenow fragment of *E. coli* DNA polymerase I, and a radioactive deoxynucleoside triphosphate, and incubated at room temperature for three to four hours. Although new DNA strands are synthesized which are complementary to the existing DNA template and which utilize the random oligonucleotides as primers, random primer DNA labelling by this technique does not substantially amplify the existing DNA. Calculations based on the data presented by Feinberg et al., supra, show that a maximum of a single copy of DNA synthesis occurs during the reaction period of many hours.

The PCR has become widely used as a nucleic acid amplification technique (Mullis, K. et al., *Cold Spring Harbor Symp. Quant. Biol.* 51:263-273 (1986); Erlich H. et al., EP 50,424; EP 84,796 EP 258,017, EP 237,362; Mullis, K., EP 201,184; Mullis K. et al., U.S. Pat. No. 4,683,202; Erlich H., U.S. Pat. No. 4,582,788; and Saiki, R et al., U.S. Pat. No. 4,683,194). Although the PCR provides a method for achieving the amplification of a particular nucleic acid region in an unfractionated sample, the method has several disadvantages. First, PCR requires the identification and use of two different oligonucleotide probes, both of which must be highly specific for each sequence to be amplified. Sequence-specific oligonucleotide probes represent a considerable expense because they usually must be synthesized by chemical methods and because they are used in relatively large amounts in each reaction in order to maximize the efficiency of the amplification procedure.

Secondly, PCR is usually performed using sophisticated programmable equipment. The products of each extension reaction in PCR ordinarily are separated from their template strands by heat denaturation. The multiple (for example, 30-70) cycles of heating, rehybridization and primer extension may be manually performed, but more commonly, programmable temperature control devices are employed.

Thirdly, the PCR reaction is usually run in conjunction with a thermostable DNA polymerase. The combination of synthetic oligonucleotide primers, sophisticated equipment, and unusual DNA polymerase means that PCR, while powerful, is expensive.

Variations on the PCR technique have been reported which only partially address some of these problems. For example, Loh et al., *Science* 243:217-200 (1988), discloses a PCR technique which requires that the sequence of only one end of the target be known.

In many cases, sequence information about a target is not known although a clone to that target is available. Also, in some cases, the sequence may be highly variable, so that it is difficult if not impossible to identify target-specific oligonucleotide probes.

Thus, a need exists for a method capable of amplifying the levels of a nucleic acid sequence wherein such method does not depend on the availability of sequence information or the identification of target-specific oligonucleotides. Further, it is desirable that such a method would not require complex sample processing equipment or technical manipulation during the amplification. It is also desirable that the method have low background levels, i.e. it should polymerize little or no nucleotides in the absence of a polynucleotide target.

SUMMARY OF THE INVENTION

The present invention represents simple, but fundamental, modifications to methods utilizing oligonucleotide priming of template directed nucleic acid synthesis, with the important result that the nucleic acids which are present in a sample are substantially amplified in a short period of time. The present invention is simple, inexpensive to perform, does not require special equipment, and can be applied with minor modifications to the amplification of RNA sequences as well as DNA sequences.

According to this invention, Random Priming Amplification (RPA), a process for the amplification of template nucleic acid sequences present in a sample is described, wherein knowledge of a nucleic acid sequence is not required.

Specifically, the present invention provides a process for the amplification of a nucleic acid template in a sample, which process comprises synthesis of nucleic acid sequences in a randomly primed, but template dependent manner. The process includes the steps of priming single-stranded template nucleic acid strands with an excess of random oligonucleotide primers and incubating the single-stranded template nucleic acid strands and excess random oligonucleotide primers in the presence of excess amounts of an inducing agent, a strand displacement agent, and nucleoside triphosphate substrates to randomly amplify nucleic acid strands.

DETAILED DESCRIPTION OF THE INVENTION

The present invention provides a method for amplifying nucleic acid polymers in a "sample". Such "samples" may include biological samples derived from a human or other animal source (such as, for example, blood, stool, sera, urine, saliva, tears, biopsy samples, histology tissue samples, PAP smears, moles, warts, etc.) including samples derived from a bacterial or viral preparation, as well as other samples (such as, for example, agricultural products, waste or drinking water, milk or other processed foodstuff, air, etc.). The template nucleic acid molecules may be either DNA or RNA and may be either homologous to the source or heterologous to the source or both. For example, amplification of a human tissue sample infected with a virus may result in amplification of both viral and human sequences.

Macromolecular entities that contain nucleic acid other than double-stranded DNA, or single-stranded DNA, such as single-stranded RNA, double-stranded RNA, or mRNA are capable of being amplified by the method of the invention. For example, the RNA genomes of certain viruses can be converted to DNA by reaction with reverse transcriptase (Maniatis, T. et al., *Molecular Cloning (A Laboratory Manual)*. Cold Spring Harbor Laboratory, 1982; Noonan, K. F. et al., *Nucl. Acids Res.* 16:10366 (1988)). The product of the reverse transcriptase reaction may then be amplified according to the invention.

"Template" as used herein refers to a nucleic acid polymer, such as DNA or RNA, which is capable of serving as a substrate for the synthesis of a complementary nucleic acid strand. Nucleic acid templates may be in a double-stranded or single-stranded form. However, if the nucleic acid is double-stranded at the start of the amplification reaction it may first be treated to denature the two strands into a single-stranded, or partially single-stranded, form. Methods are known to render double-stranded nucleic acids into single-stranded, or partially single-stranded, forms, such as heating, preferably by heating to about 90°-100° C. for about 1 to 10 minutes, or by alkali treatment, such as a pH greater than 12.

For the RPA methods of the invention it is necessary that the template nucleic acid be in a configuration that is capable of functional apposition to the primers and of undergoing strand displacement in response to the presence of the strand displacement agent. By "functional apposition" is meant apposition such that the pairing of the primer and template results in a construct which is capable of being utilized by a DNA polymerase for the synthesis of DNA in a primed and template dependent manner.

By nucleic acid synthesis in a "template dependent manner" is meant synthesis wherein the sequence of the newly synthesized strand of nucleic acid is dictated by complementary base pairing to the sequence of a template nucleic acid strand.

"Amplification" as used in the methods of the invention, refers to an increase in the amount of nucleic acid sequence, wherein the increased sequence is the same as or complementary to the pre-existing nucleic acid template. For purposes of this invention, "substantial amplification" is defined as greater than about threefold amplification of template sequences. For example, an amplification reaction which yields 300 pg of a DNA sequence the same as or complementary to a template, from an initial amount of 100 pg of template, is a substantial amplification.

An "excess" of primer, inducing agent, strand displacement agent, and nucleoside triphosphate substrates refers to an amount of each component sufficient to support amplification of template nucleic acid in a manner such that substantial amplification is not limited by the concentration of that component.

An "inducing agent" as used herein refers to a chemical, physical, or biological agent capable of promoting polymerization of nucleotides into nucleic acid polymers in a template-directed manner. DNA polymerases are inducing agents according to the invention. DNA polymerases begin the synthesis of a new nucleic acid chain by adding nucleotides to the hydroxyl group at the 3'-end of a pre-existing RNA or DNA primer using a pre-existing DNA strand as the template. A preferred inducing agent is the large proteolytic fragment of the DNA polymerase I of the bacterium *E. coli*, commonly known as Klenow polymerase. Other DNA polymerases, such as *E. coli* DNA polymerase I, and bacteriophage T7 DNA polymerase, may also be used to perform RNA.

It is necessary to provide to the assay mixture an amount of required cofactors such as $Mg^{++}$, and dATP, dCTP, dGTP, dTTP, ATP, CTP, GTP, UTP or other nucleoside triphosphates, herein called "triphosphate substrates", in sufficient quantity to support the degree of amplification desired. The amount of deoxyribonucleotide triphosphates substrates required for substantial DNA amplification by RPA using the Klenow polymerase typically will be in the range of about 50 $\mu$M to about 2 mM, preferably initially 400 $\mu$M concentration at the start of the amplification. Nucleoside triphosphateanaloguescan be substituted or added to those specified above, provided that the base pairing, polymerase, and strand displacing functions are not adversely affected to the point that the amplification does not proceed to the desired extent.

"Strand displacement" as used herein refers to the phenomenon in which a chemical, physical, or biological agent, for example, a DNA polymerase, causes the dissociation of a base-paired nucleic acid from its complementary strand in a 5'-to-3' direction in conjunction with, and in close proximity to, template-directed nucleic acid synthesis. Strand displacement begins at the 5'-end of a base-paired nucleic acid sequence and proceeds in consequence of nucleic acid synthesis immediately 5'-to the displacement site. Both the newly synthesized and displaced nucleic acids have the same base sequence, which is complementary to the template nucleic acid strand. The strand displacement activity may reside on the same molecule with another activity such as nucleic acid synthesis and especially DNA synthesis, or it may be a separate and independent activity. DNA polymerases such as *E. coli* DNA polymerase I, the Klenow fragment of DNA polymerase I, the bacteriophage T7 DNA polymerase, and the bacteriophage T5 DNA polymerase, are enzymes which possess both polymerase activity and strand displacement activity. Agents such as helicases may be used in conjunction with inducing agents which do not strand displace, in order to produce the effect of strand displacement, that is, displacement of a nucleic acid strand coupled to the synthesis of a nucleic acid strand of the same sequence. For a discussion of strand displacement see Kornberg, A., *DNA Replication* W.H. Freeman & Co., San Francisco, Calif., 1980.

As used herein, "priming" or "to prime" refers to the apposition of an oligonucleotide or nucleic acid to a template nucleic acid, whereby said apposition enables an inducing agent to polymerize nucleotides into a nucleic acid which is complementary to the template nucleic acid.

As used herein, the term "primer" refers to an oligonucleotide, preferably an oligodeoxynucleotide, with a random sequence. By "random sequence" is meant a sequence not designed to be directed to a specific sequence in the nucleic acid sample to be amplified. In accord with this invention, a primer possesses a free 3'—OH group which upon apposition to the nucleic acid template is recessed relative to the 5'-end of the template and thus is capable of acting as a site of initiation of the synthesis or polymerization of a nucleic acid polymer, the sequence of which is complementary to the template strand, in the presence of nucleotides and an inducing agent such as DNA polymerase and at a suitable temperature and pH.

The primer is preferably single stranded for maximum efficiency in amplification, but may alternatively be double stranded. If double stranded, the primer may be first treated, for example, by heating at a temperature sufficient to separate the strands, before being used to prepare extension products (for example, see *Nucleic Acid Hybridization. A Practical Approach.* B. D. Hames and S. J. Higgins, eds., IRL Press, Washington, 1985), preferably to about 90°-100° C. for about 1 to 10 minutes.

By primers of "random" sequence is meant that the positions of apposition of the primers to the nucleic acid template are substantially indeterminate with respect to the nucleic acid sequence of the template under the reaction conditions used in the methods of the invention. Methods for estimating the frequency at which an oligonucleotide will appear in a nucleic acid polymer are described in Volinia, S. et al., *Comp. App. Biosci.* 5: 33-40 (1989). It is recognized that the sequences of random primers may not be random in the mathematic sense. Chemically synthesized random primers will be random to the extent that physical and chemical efficiencies of the synthetic procedure will allow. Random primers derived from natural sources will be less random, due to favored arrangements of bases in the source organism. Random primers derived from the homologousnucleic acid polymer whose amplification is desired may still fall within the definition of random. Oligonucleotides having defined sequences may satisfy the definition of random if the conditions of their use cause the locations of their apposition to the template to be indeterminate. All these examples of primer types are defined to be random so long as the positions along the template nucleic acid strand at which the primed extensions occur are largely indeterminate.

If the primer is not of random sequence, its sequence must be of sufficient diversity to prime at multiple sites along the template nucleic acid sequence, since the degree of amplification may be proportional to the number of priming sites. Nonstringent conditions may be used which will allow some primers to non-specifically or randomly appose at many sites on the nucleic acid template where otherwise, under stringent hybridization conditions, those primers would only hybridize to a specific site (for example, see *Nucleic Acid Hybridization, A Practical Approach.* B. D. Hames and S. J. Higgins, eds., IRL Press, Washington, 1985).

It is not necessary that apposition of the primer to the template be at the site of a sequence identical to that of the primer. A primer which apposes to the template with some mismatch is within the scope of the invention if the mismatched primer-template structure can still serve as a site from which to enzymatically synthesize extension products of the primer which are complementary to the template. One of ordinary skill in the art, without undue experimentation, will be able to design many reaction conditions, both stringent (allowing only a perfect complementary sequence match between the primer and the template) and nonstringent (allowing some mismatch in the primer-template pairing) within the scope of the methods of the invention (*Nucleic Acid Hybridization, A Practical Approach.* B. D. Hames and S. J. Higgins, eds., IRL Press, Washington, 1985).

Random oligodeoxyribonucleotides 8 bases long are preferable using the conditions described here. However oligoribonucleotides, or oligodeoxyribonucleotides, other than 8 bases long may also be used, such as 4-mer, 5-mer, 6-mer, 7-mer, 9-mer, 10-mer, and up to 50 bases. The primer must be of sufficient length to prime the synthesis of extension products in the presence of the inducing agent. The optimal length of the primers will depend on many factors, including the inducing agent used, and the purpose of the amplification. For diagnostic applications using the Klenow fragment of *E. coli* DNA polymerase I, primers of about 8 nucleotides are preferred.

The sequence of the primer can either comprise one or more of the deoxyribonucleoside DNA bases dA, dT, dC, or dG; or one or more of the ribonucleoside RNA bases A, U, C, or G; or one or more analogues of an afore cited base, e.g. I, dI, or dU (inosine, deoxyinosine, or deoxyuridine). For the purposes of the present invention, deoxyuridine and thymidine are considered to be equivalents and ribothymidine and uridine are considered to be equivalents, as long as the polymerizing agent can use primers containing the nucleotide used. Primers may be derivatized with chemical groups to optimize their performance or to facilitate the characterization of amplification products. For example, primers substituted with biotin can be synthesized by known techniques (Murasagi, A. et al., *DNA* 3:269 (1984); Cook, A. F., et al., *Nucleic Acids Res.* 16:4077 (1988)), which might be desirable in the quantification of the amplification products. Primers may also contain reactive sites for enzymes, for example cleavage sites for restriction endonucleases or promoter sites for RNA polymerases. Such sites would allow, for example, cloning of amplification products or transcription of amplification products.

Primers may be synthetically made, for example, as described in *Oligonucleotide Synthesis, A Practical Approach.* M. J. Gait, ed., IRL Press, Washington, 1984, or primers may be generated by cleavage or degradation of the nucleic acid of a natural source. Such random primers prepared from naturally occurring nucleic acid are also useful in the RPA methods described here and may be prepared from naturally occurring DNA or RNA that was either homologous or heterologous to the source of the nucleic acid which serves as the initial template for the first round of DNA synthesis. Primers from natural DNA or RNA can be prepared by degradation of the DNA to small fragments, preferable fragments of 5-50 bases or base pairs. Natural DNA or RNA may be degraded by a variety of processes, for example, enzymatically with DNase or RNase. Primers may also be purchased commercially, for example, the random primer supplied by P-L Biochemicals or by Pharmacia or the linkers sequences commonly sold for cloning purposes.

In vivo, during the DNA replication process, primers consisting of RNA are synthesized by RNA polymerases or primases on the DNA template for use by DNA polymerases. Especially with a partially denatured DNA template, RPA may also occur in a reaction in which the necessary primers are synthesized in the reaction tube itself, for example, by addition of an RNA polymerase or primase and the four ribonucleoside triphosphates under conditions such that synthesis of the primers used in the amplification reaction occurs in concert within the RPA assay. In this embodiment, the random nature of the priming event is dictated by the nature of RNA polymerase or primase binding along the template.

Following the above-described procedures, the denatured, single-stranded nucleic acid sequences of the sample are incubated, under conditions conducive to priming, DNA polymerization, and strand displacement in the presence of the primers, the inducing agent, the strand displacement agent, nucleoside triphosphates, and the co-factors discussed above. Denaturation of the nucleic acid sequences in the sample to be amplified is recommended for the first round of RPA synthesis to ensure that double-stranded structure and other secondary structures such as hairpins are minimized in the sample.

The apposition of the primer to a template DNA will produce a duplex molecule having a recessed 3'-hydroxyl end, and thus will create a substrate for DNA polymerase. Thus, since the reaction mixture contains the inducing agent, a strand-displacement agent, deoxyribonucleotides and other necessary co-factors, template-directed extension of the apposed primer in the sample will occur. The primer extension product will have a nucleic acid sequence complementary to the target sequence.

Conditions or agents which increase the rate or extent of priming, primer elongation, or strand displacement, may increase the extent of the amplification obtained with RPA. For instance, the addition of helicases or single-stranded nucleic acid binding proteins may increase the strand displacement rate of a DNA polymerase, or may allow the use in RPA of a DNA polymerase that does not ordinarily give substantial amplification.

In another embodiment, RPA is performed in a repeated manner on a nucleic acid template. For example, sequences amplified by RPA may be purified (for example, by gel electrophoresis, by column chromatography, by affinity chromatography, or by hybridization) and the fractions containing the purified products may be subjected to further amplification by RPA.

Not all the DNA present in the sample after RPA may arise from template-directed DNA synthesis. It is known that DNA polymerases such as DNA. polymerase I of $E.$ $coli$ and the Klenow fragment of DNA polymerase I can utilize primers and deoxynucleoside triphosphates to synthesize DNA sequences, even relatively large, substantially duplex, DNA structures, in the absence of added template DNA (Schachman, H. K., et al., $J.$ $Biol.$ $Chem.$ 235:3242 (1960); Setlow, P., et al., $J.$ $Biol.$ $Chem.$ 247:224 (1972)). This template-independent "de novo" synthesis may occur in samples simultaneously with the RPA methods of the invention. Depending on the amount of input template DNA added to the RPA methods of the invention, most of the DNA found to be synthesized at the end of the reaction may in fact be the result of de novo synthesis. In a standard RPA reaction (15 $\mu$g primers, 25 $\mu$g dNTPs, 20 units Klenow fragment of $E.$ $coli$ DNA polymerase I, in 50 $\mu$l at 37° C. for 2 h.), 10-12 $\mu$g of de novo DNA product is synthesized, which represents about half of the RPA reaction synthetic capacity, based on mass of dNTPs incorporated into polymers. Notwithstanding the occurrence of de novo DNA synthesis, the RPA methods of the invention proceed so as to give substantial amplification of added template DNA.

De novo synthesis can be reduced by using special random primers. These random oligonucleotide primers are made of ribonucleotides or deoxyribonucleotides having three bases chosen from the four standard bases: A, T, C, and G. These primers also have a non-standard base, i.e. a base that is not A, T, C, or G. (Note that for the purposes of the present invention, the base U and the base T are considered equivalents. Therefore, one can choose three bases from the group A, T, C, and G or one can choose three bases from the group A, U, C, and G.) By using these special primers, de novo amplification may be reduced relative to the level observed with random primers comprising the standard bases A, T, C, and G. As exemplified herein, de novo synthesis was decreased by using random oligonucleotide primers made of deoxyribonucleotides having A, T, C, and I as bases, i.e. the non-standard base was I (i.e. the non-standard nucleoside was deoxyinosine dI). In other words, in these primers, which were random octamers (8-mers), dI was substituted for deoxyguanosine (dG). dI can base pair weakly via two hydrogen bonds with a number of different bases. It forms only two hydrogen bands instead of three; de novo synthesis which emerges from primer-primers interaction is attenuated or eliminated. Not all non-standard bases will decrease de novo synthesis, however, bases other than I can be tested without undue experimentation, other bases or nucleoside that can be tried include hypoxanthine, bromodeoxyuridine (BrdU), and the like.

RPA may be adapted to permit its use in identifying or detecting the presence of any desired nucleic acid molecule. These properties render the assays of the present invention suitable for applications in medical diagnostics, agricultural, environmental and foodstuff monitoring, or any other use requiring the detection of specific DNA or RNA at low concentration.

The assays of the present invention have substantial utility in the fields of epidemiology, food science and waste management. For example, samples of air, water or food (such as milk, dairy products, meat, poultry, etc.) can be incubated in accordance with the methods of the present invention in order to assess and identify the presence of pathogenic bacteria (such as $S.$ $typhosa,$ $M.$ $tuberculosi,$ etc.), yeasts, protozoa, nematodes (such as the causal agent of heartworm, trichinosis, malaria, etc.) or viruses (such as those responsible for hepatitis, influenza, shipping fever, etc.). The nucleic acid present in the sample can be amplified to a point that probe sequences complementary to characteristic sequences of the suspected pathogens can be used with a high degree of assurance for the detection of their presence in the sample.

It may be desirable to conduct purification schemes directed to enriching the sample in template nucleic acid prior to conducting RPA. Purification techniques are well-known and would include any technique for nucleic acid purification, either manual or automatic for example, see Maniatis, T. et al., *Molecular Cloning (A Laboratory Manual)*. Cold Spring Harbor Laboratory, 1982; and, Landegren, U. et al., *Science* 242:229-237 (1988).

The RPA assay of the present invention is especially facilitated and enhanced by the use of "kits," whose components are especially adapted to be used with one another. Such kits will typically provide a carrier, compartmentalized to receive in close confinement a series of containers containing the random primers, the inducing agent, the strand separation agent, and the deoxynucleotides and buffers and salts necessary to pursue a particular assay. Thus for example, a "kit" designed to detect papilloma virus will contain in addition to the reagents listed above, a probe for detecting the papilloma virus. Likewise, similar kits can be prepared to detect the presence of a virus or bacterium for which a probe is available, especially, for example, HIV, bacterial contamination of foods, and yeast infection, etc.

The invention also contemplates the characterization of such amplified molecules. The amplified molecules obtained by the practice of the invention can be analyzed through the use of any of a variety of methods well known in the art in order to further characterize their sequence or nature. For example, such amplified molecules can be sequenced, restriction digested, electrophoresed, cloned, or hybridized against a reference nucleic acid molecule. Such information can be used in diagnostics, and for other uses.

Sequences amplified by the methods of the invention can be further evaluated, detected, cloned, sequenced and the like either in solution or after binding to a solid support, by any method usually applied to the detection of a specific DNA sequence such as PCR, oligomer restriction (Saiki, R. K. et al., *Bio/Technology* 3:1008-1012 (1985)), allele-specific oligonucleotide (ASO) probe analysis (Conner, B. J., et al., *Proc. Natl. Acad. Sci. USA* 80:278 (1983)), oligonucleotide ligation assays (OLAs) (Landegren, U. et al., *Science* 241:1077 (1988)), and the like. Molecular techniques for DNA analysis have been recently reviewed (Landegren, U., et al., *Science* 242:229-237 (1988)).

The advantages of the methods of the invention include the ability to amplify nucleic acids without prior knowledge of their sequence, in a system that does not require complex handling or automation or repeated intervention on the part of the technician performing the analysis. Repeated cycles of heating at various temperatures are not required to denature double-stranded nucleic acids and re-anneal the primers to the template as are required in PCR analysis.

The methods of the invention are especially useful for the amplification of regions of a nucleic acid which are prone to rearrange or which are highly variable due to a high mutational frequency. Such regions include genes such as the immunoglobulin genes, receptor genes, and genes encoding highly variable viral coat sequences. Thus, by the methods of the invention, viral sequences that are randomly integrated in a genome or otherwise present in a cell and which have a tendency to have a high mutational rate can be amplified for further study.

In a preferred embodiment both the probe and the template are in solution. In another embodiment, the amplification methods of the invention may be performed wherein the primers are attached to a solid phase such that attachment does not interfere with their ability to prime DNA synthesis. The advantage of this embodiment is that all the amplified products would be covalently bound to a solid phase support, thus simplifying their isolation, characterization and use in, for example, diagnostic assays.

Attachment of the primer to the solid phase may occur through the use of a non-nucleic acid linker to separate the primer from the solid phase backbone and thus facilitate the steric flexibility of the primer in the apposition step. Further, use of a primer containing a unique restriction endonuclease site, or other enzyme recognition site, would facilitate removal of the amplified nucleic acid product, for example, under conditions where it is desired clone or transfer the amplified product to another environment. Use of a proteinaceous linker comprising a recognition site of a protease would also allow release of the bound product. Another advantage of this embodiment is that any tendency of linkers, especially those which are palindromic sequences, to form double-stranded forms with other linkers will be minimized.

Further, the methods of the invention are applicable to an embodiment wherein the sample's nucleic acid template is bound to a solid phase and the primers are in solution. The advantages of this embodiment include the ability to use fixed paraffin tissue samples such as are often taken for histological analysis in clinical settings for the amplification procedures of the invention.

Having now generally described this invention, the same will become more readily understood by reference to specific examples included herein for purposes of illustration only, and are not intended to be limiting unless otherwise specified.

EXAMPLE 1

An 8-kilobase sequence of human papilloma virus (HPV) type 18 DNA was excised from a plasmid vector with the endonuclease EcoR I. Following dilution in buffer, 100 pg quantities of DNA were added to separate 50 µl reactions containing RPA buffer (200 mM HEPES/NaOH pH 6.8, 50 mM Tris/HCl pH 6.8, 10 mM 2-mercaptoethanol, 5 mM magnesium chloride, 400µg/ml bovine serum albumin, all final concentrations), deoxynucleotides (dATP, dCTP, dGTP, and dTTP, all 400 µM final concentrations), and random 6-mer, 7-mer, 8-mer, 9-mer or 10-mer oligodeoxynucleotides (Synthetic Genetics, Inc.). The amount of each primer which was added to the reaction was normalized for the molecular weight of the primer so as to provide equal moles of 3'-ends in every reaction; therefore, 15 µg of 6-mers, 17.6 µg of 7-mers, 20.1 µg of 8-mers, 22.6 µg of 9-mers or 25.1 µg of 10-mers were added to the appropriate reactions. Parallel reactions containing random primers but without any added papilloma virus DNA were also prepared. All reactions were placed in a boiling water bath for 10 minutes to denature the human papilloma virus 18 DNA, then quick-chilled on ice for five minutes. Ten units of Klenow DNA polymerase (1.6 µl) were added to all tubes, and the tubes were incubated in water baths at either 37° C. or 45° C. After two hours an additional ten units of Klenow polymerase were added to all reactions. After four hours aliquots of each reaction, as well as known quantities of the input EcoR I-cut HPV 18 DNA (as standards) were diluted into 0.5M sodium hydroxide and filtered onto Biodyne B nylon membrane (Pall Corporation). The membrane was probed to determine the extent of the amplification achieved using a $^{32}$p-RNA probe specific for human papilloma virus type 18. Comparison of the intensities of standard spots with the intensities of the spots produced by the various amplification products, combined with the known dilution factors, allowed estimations of the degrees of amplification. The "dot blot" analysis showed 37° C. to result in optimum amplification if a 6-mer or 7-mer random primer was used, and 45° C. to result in optimum amplification if a larger random primer was used. The amplifications achieved after four hours at 37° C. were about 2,500-fold and 7,500-fold for the 6-mer and 7-mer, respectively. At 45° C., after four hours, the 8-mer, 9-mer, and 10-mer primers produced amplifications of about 15,000-fold, 5,000-fold and 3,000-fold, respectively. These values should be considered to be accurate only to within about two-fold since they are derived from comparison of the intensities of dark regions on the X-ray film for dilutions of both the reaction products and the DNA standards. Reactions from which HPV 18 DNA was omitted did not give any signal on the dot blot.

EXAMPLE 2

The time course and specificity of the amplification reaction were examined. Fifty microliter reactions containing RPA buffer, nucleotides, and random 8-mers, all as above, and either 100 pg of linear HPV 18 DNA, or no template DNA, were boiled, cooled, and incubated at 45° C. with 10 units of Klenow polymerase as above. At times one hour, two hours, four hours, eight hours, or overnight (approximately 16 hours), individual reactions were frozen. At the completion of the time course, three aliquots of each reaction were removed. One set of aliquots was applied to a 0.9% agarose, 2 μg/ml ethidium bromide, Tris acetate/EDTA gel (Maniatis, T. et al., *Molecular Cloning (A Laboratory Manual)*, Cold Spring Harbor Laboratory, 1982;) and electrophoresed and photographed. A second set of aliquots was assayed for the amount of DNA present. Aliquots were added to buffer containing 0.1 μg/ml of the fluorescent dye Hoescht 33258, and the fluorescence of each dilution was determined and compared to that of standard DNA using a DNA fluorometer (Hoefer Scientific, San Francisco, Calif.). A third set of aliquots was diluted into 0.5N NaOH, filtered onto BioDyne B nylon membrane, and probed with $^{32}$p-HPV 18 RNA.

The dot blot analysis showed an amplification time course of approximately 500-fold, 1,000-fold, 5,000-fold, 5,000-fold, and 8,000-fold at the one hour, two hour, four hour, eight hour, and overnight time points, respectively.

The agarose gel analysis showed DNA synthesis increasing with time, from amounts near the lower limit of detectability at one hour, easily visible DNA at two hours, and massive synthesis at four hours, eight hours, and overnight. The bulk of the visible DNA migrated on the gel with a size corresponding to less than 500 base pairs. Visibly, there was no difference in the amount of DNA synthesized between those reactions that contained 100 pg of HPV 18 template DNA and those that did not contain any added template DNA. The "de novo" reaction (supra) observed by Kornberg and others (Schachman, H. K. et al., *J. Biol. Chem.* 235:3242 (1960); Burd, J. F., et al., *J. Mol. Biol.* 53:435 (1970)) is presumably able to utilize oligonucleotides within the random 8-mers in some nonconventional way to synthesize much larger DNA. At the one-hour time point, both the HPV 18 sample and no template reactions contained DNA in amounts near the lower limit of the fluorometric assay, corresponding to about 0.25μg total DNA synthesized per reaction. At two hours, four hours, eight hours, and overnight, the reactions containing input HPV 18 DNA contained 2.25, 11.25, 13.25, and 18.75 μg DNA, while those reactions that did not receive any input template DNA contained about 1.5, 8.25, 10.25, and 14.25 μg of DNA (average of two reactions).

EXAMPLE 3

The RPA method was demonstrated on hepatitis B DNA purified from human serum. Five hundred nanograms of linear plasmid DNA containing the cloned genome of subtype adw DNA (Hartley, J., et al., *Gene* 49:295 (1986)) were added to 78 μl of human serum and then extracted by a method shown to purify HBV DNA from virions contained in serum (ibid.). Aliquots of the recovered DNA either were diluted directly into 0.5N NaOH or were diluted, placed in RPA buffer, boiled, cooled, amplified as above, and diluted into NaOH. The sodium hydroxide dilutions were filtered onto BioDyne B membrane and probed with HBV $^{32}$p RNA probe. From the known dilution factors, the HBV DNA recovered from the serum was amplified about 1,000 times in the standard two-hour, 45° C. RPA amplification procedure.

Amplification conditions may be varied to enhance RPA. For example, amplification at least as good as, if not better than the 1000-fold amplification found after 2 hr at 45° C. may be obtained by raising the pH of the reaction buffer to 7.1, omitting the HEPES/NaOH, and adding 30 U Klenow polymerase instead of 10 U.

EXAMPLE 4

The RPA method was applied in a kit format with containers containing the random primers, the inducing agent, the strand separation agent, and the deoxynucleotides and buffers and salts and a probe specifically designed to detect papilloma virus. Linear cloned HPV 16 DNA (0 to 1,000 fg) (the sample to be detected) was added to 100 μl denaturation buffer (1M guanidine HCl, 10 mM Tris HCl pH 8.0, 1 mM EDTA, 0.05% sodium azide) from container No. 1 and denatured by the addition of 20 μl of 0.5M NaOH from container No. 2. The NaOH was neutralized by adding 60 μl of neutralization buffer (6% polyacrylic acid, 750 mM sodium citrate, 250 mM citric acid, 1M potassium phosphate, 5 mM EDTA, 0.3% Tween 20, 0.05% sodium azide) from container No. 3. Capture beads (10 μl) from container No. 4 were added which consisted of paramagnetic beads of approximately 4 microns diameter (Dynal) to which 20 fmol of HPV 16 capture oligonucleotide (shown in Table I) had been attached through their 3'-ends.

TABLE I

| HPV Capture Oligonucleotide Sequence |
|---|
| 5'-ACGTTTTTTG CGTTTAGCAG TTGTAGAGGT- |

TABLE I-continued

HPV Capture Oligonucleotide Sequence

-AGATGAGGTG GTGGGTGTAG CTTTTCGTTT-

-TCCTAATGTA AATTTTGGTT-3'

The beads were incubated in the reaction for 30 minutes at 65° C. to capture one strand of the HPV target. Beads were washed using magnetic separation and then 50 μl of RPA reaction mixture (RPA buffer from container No. 5, containing 15 μg of random 8-mers from container No. 6, and 10 units Klenow polymerase from container No. 7) were added to the beads. The mixture was incubated at 45° C. for two hours, then 10 μl of 5M NaOH from container No. 8 were added to denature the RPA products. After two minutes at room temperature, 30 μl of neutralization buffer (supra) from container No. 3 were added. The denatured RPA products were hybridized to 10 ng of HPV 16 RNA in 5 μl of water from container No. 9 at 65° C. for one hour. Excess unhybridized RNA was digested by addition of 200 μl of 10 μg/ml RNAase A from container No. 10 in wash buffer (100 mM Tris HCl pH 7.5, 600 mM NaCl, 0.25% Tween 20) from container No. 11. RNA:DNA hybrids were captured on magnetic beads (supra) coated with antibody specific for RNA:DNA hybrids (Boguslawski, S. J., et al., *J. Immunol. Methods* 89:123 (1986)) from container No. 12. The beads were washed twice with wash buffer (container No. 11), once with 100 mM Tris HCl pH 7.5, 0.15M NaCl, 0.25% Tween 20, from container No. 13, and then 50 μl of RNAse III (10 μg/ml in 40 mM Tris HCl pH 7.5, 4 mM MgCl$_2$) from container No. 14, were added and incubated for 15 minutes at room temperature to degrade captured double-stranded RNA. The captured RNA:DNA hybrids were then reacted with anti-RNA:DNA antibody conjugated to alkaline phosphatase from container No. 15, followed by six washes with wash buffer (container No. 11), and the alkaline phosphatase activity was detected with the "ELISA Amplification System" (BRL cat. no. 9589SA, Life Technologies, Inc., Gaithersburg, Md.). Table II shows the results. Ten femtograms (fg) of HPV 16 DNA could be detected. It is not necessary to provide all the compartments of the kit as defined in the example above. Many of the reagents and buffers are commonly available in laboratories of ordinary skill in the art, such as, for example, NaOH, RNase and wash buffers.

TABLE II

| Input HPV 16 DNA | Optical Density (490 nm) |
|---|---|
| 1000 fg | 7.8; 8.0 |
| 100 fg | 5.8; 4.7 |
| 25 fg | 1.58; 1.66 |
| 10 fg | 0.96; 1.05 |
| 1 fg | 0.599; 0.707 |
| 0 fg | 0.475; 0.521 |

The performance of the RPA method was determined at varying concentrations of triphosphate substrates. One hundred picogram amounts of linear HPV type 18 plasmid DNA (supra) were mixed with RPA buffer, random 8-mers, and the following concentrations of nucleoside triphosphates: a) 400 μM each of dATP, dGTP, dTTP, and dCTP; b) 150 μM each of dATP, dGTP, dTTP, and dCTP; c) 50 μM each of dATP, dGTP, dTTP, and dCTP; or, d) the triphosphate concentrations recommended in the probe synthesis method of Feinberg and Vogelstein (vide supra), that is, 20 μM each dATP, dGTP, and dTTP and 0.5 μM dCTP. The reactions were boiled and cooled as above. Ten units of Klenow polymerase were added and the reactions were incubated at 45° C. for two hours. The reactions were analyzed by the dot blot procedure. The autoradiograph of the dot blot showed amplification of about 800-fold in reaction (a); 300-fold in reaction (b); 50-fold with reaction (c); and no detectable amplification with reaction (d). These results demonstrate that nucleotide concentrations have a marked effect on the amplifications obtained with the RPA method.

EXAMPLE 6

The effect of the concentration of random 8-mers on the RPA method was investigated. One hundred picogram amounts of linear HPV type 18 plasmid DNA were mixed with RPA buffer, 400 μM nucleoside triphosphates, and random 8-mer primers in amounts of a) 30 μg, b) 15 μg, c) 7.5 μg, d) 3.7 μg, or e) 1.9 μg per 50μl reaction volume. After boiling and cooling, 30 units of Klenow polymerase were added to each reaction and each reaction was incubated at 45° C. for 2 hours. Aliquots of each reaction were analyzed by dot blot analysis. The autoradiograph showed amplifications of about 2000-fold with (a), 2500-fold with (b), 1500-fold with (c), 300-fold with (d), and 40-fold with (e). These results show that the optimum amount of synthetic random 8-mers is approximately 15 μg per 50 μl reaction.

EXAMPLE 7

The ability of inosine-containing primers to decrease de novo synthesis was investigated. Reactions were performed in 50 μl volumes in 0.5×RPA buffer (0.5×RPA buffer 25 mM Tris.HCl, pH 7.1; 2.5 mM MgCl$_2$; 5 mM β-mercaptoethanol; 200 μg/ml acetylated bovine serum albumin). Each sample contained 20 units of the Klenow fragment of *E. coli* DNA polymerase I and target samples received 1 pg linearized HPV 16 plasmid DNA which had been denatured by boiling in 0.5×RPA buffer for 5 min. Incubations were performed at 37° C. or 25° C., and samples were removed and diluted into 50μl 20 mM sodium ethylene diamine tetraacetic acid (Na$_2$EDTA), pH 8.0, at specified times during the reaction.

Random octamer primers containing dI were chemically synthesized by Synthecell Corp. (Gaithersburg, Md.) using standard phosphoramidite chemistry. During each cycle of polymerization, equal-molar amounts were added of all four nucleotides: dA, dI, dC, and dT.

Random octamer primer concentration was selected based on optimal target-specific RPA output. Specifically, 5 μg of dG-containing primers and 30 μg of dI-containing primers were used for each reaction. Tests 1 and 2 were performed at 37° C. and 25° C., respectively. In addition, different preparations of RPA buffer were employed for test 1 and test 2.

RPA products were quantified by Hoechst 33258 dye intercalation followed by fluorometric detection. Reagents were prepared according to the manufacturers instructions. Quantitation was performed using a Model TKO 100 DNA Fluorimeter (Hoeffer Scientific, San Francisco, Calif.). DNA standard was "1 Kb DNA Ladder" (BRL cat. no. 5615SA, Life Technologies, Inc., Gaithersburg, Md.). Target-specific DNA synthesis was determined by a dot-blot hybridization followed by quantitation with a Betascope 603 Blot Analyzer (Betagen Corp., Waltham, Mass.) using standards containing known amounts of DNA target.

Table III depicts kinetics of target-specific, as well as de novo (total DNA) synthesis. (Different preparations of RPA buffer were employed for the two tests.) Random dI-containing octamer primers give higher target-specific HPV16 DNA amplification, albeit with slower kinetics. Additionally, target-specific DNA synthesis is evident before de novo synthesis when dI primers were used, whereas target-specific and de novo synthesis are in relatively close synchrony in the case of dG-random octamers.

TABLE III

| | Test 1, 37° C. | | |
|---|---|---|---|
| Time (hr.): | 1.5 | 3.0 | 15 |
| dG Primers: | | | |
| Total Synthesis (μg): | 3.9 | 10.8 | 18.3 |
| Specific Synthesis (pg): | 1.6 | 6.5 | 6.5 |
| dI Primers: | | | |
| Total Synthesis (μg): | 0 | 1.3 | 10.3 |
| Specific Synthesis (pg): | 0.56 | 13.0 | 44.8 |

| | Test 2, 25° C. | | | |
|---|---|---|---|---|
| Time (hr.): | 1.25 | 2.5 | 4.0 | 15 |
| dG Primers: | | | | |
| Total Synthesis (μg): | 0.53 | 6.3 | 9.81 | 17.4 |
| Specific Synthesis (pg): | 4 | 99 | 105 | 114 |
| dI Primers: | | | | |
| Total Synthesis (μg): | 0 | 0 | 0.4 | 22 |
| Specific Synthesis (pg): | 1.6 | 14 | 63 | 164 |

De novo synthesis competes with target for RPA reaction components (nucleotides and enzymes) and can reduce the degree of amplification attainable in a given reaction. Random primers in which dI substitutes for dG, by reducing this undesirable competition for reaction components, substantially improve the ability to amplify DNA by RPA.

It is understood that these descriptions, examples and embodiments are for illustrative purposes only, and that various modifications would be suggested within the spirit and purview of this application and the scope of the appended claims.

What is claimed is:

1. A method for reducing de novo amplification in a process for substantially amplifying template nucleic acid sequences in a sample comprising amplification of nucleic acid in a randomly primed and template dependent manner, wherein the randomly primed amplification occurs with an excess of random oligonucleotide primers that comprise ribonucleotides or deoxyribonucleotides having bases chosen from the group of A, T, C, and I,
   wherein the base U and the base T are considered exact equivalents,
   whereby de novo amplification is reduced relative to the level observed with random oligonucleotide primers comprising bases chosen from the group A, T, C, and G.

2. A method for reducing de novo amplification in a process for substantially amplifying template nucleic acid sequences in a sample in a randomly primed and template dependent manner, comprising the steps of:
   (a) priming template nucleic acid strands with an excess of random oligonucleotide primers; and
   (b) incubating said template nucleic acid strands and said excess random oligonucleotide primers in the presence of an excess of an inducing agent, a strand displacement agent, and an excess of triphosphate substrates to randomly amplify nucleic acid strands, wherein the random oligonucleotide primers comprise ribonucleotides or deoxyribonucleotides having bases chosen from the group of A, T, C, and I,
   wherein the base U and the base T are considered exact equivalents,
   whereby de novo amplification is reduced relative to the level observed with random primers comprising bases A, T, C, and G.

3. A method for reducing de novo amplification in a process for substantially amplifying template nucleic acid sequences in a sample in a randomly primed and template dependent manner, comprising the steps of:
   (a) priming template nucleic acid strands with an excess of random oligonucleotide primers wherein said primers consist of 60-mers and 10-mers; and
   (b) incubating said template nucleic acid strands and said excess random oligonucleotide primers in the presence of an excess of the Klenow fragment of DNA Polymerase I and an excess of triphosphate substrates to randomly amplify nucleic acid strands, wherein the random oligonucleotide primers comprise ribonucleotides or deoxyribonucleotides having bases chosen from the group of A, T, C, and I,
   wherein the base U and the base T are considered exact equivalents,
   whereby de novo amplification is reduced relative to the level observed with random primers comprising bases A, T, C, and G.

4. A method of reducing de novo amplification in a process for detecting a papilloma virus in a sample comprising:
   (a) substantial amplification of said papilloma virus nucleic acid sequences in said sample wherein said substantial amplification comprises a randomly primed but template dependent synthesis of papilloma virus DNA; and
   (b) detecting said papilloma virus, wherein the random oligonucleotide primers comprise an excess of ribonucleotides or deoxyribonucleotides having bases chosen from the group of A, T, C, and I,
   wherein the base U and the base T are considered exact equivalents,
   whereby de novo amplification is reduced relative to the level observed with random primers comprising bases A, T, C, and G.

5. A kit for reducing de novo amplification while substantially amplifying nucleic acid sequences in a sample in a randomly primed and template dependent manner, comprising a carrier being compartmentalized to receive in close confinement therein one or more containers wherein:
   (a) a first container or series of containers contains random oligonucleotide primers;
   (b) a second container contains an inducing agent;
   (c) a third container or series of containers contains triphosphate substrates; and
   (d) a fourth container or series of containers contains buffer for reconstituting or diluting components of said kit, wherein the random oligonucleotide primers comprise ribonucleotides or deoxyribonucleotides having bases chosen from the group of A, T, C, and I,
   wherein the base U and the base T are considered exact equivalents,
   whereby de novo amplification is reduced relative to the level observed with random primers comprising bases A, T, C, and G.

* * * * *